(12) United States Patent
Bielik et al.

(10) Patent No.: US 6,728,644 B2
(45) Date of Patent: Apr. 27, 2004

(54) METHOD EDITOR

(75) Inventors: Robert Bielik, Balinge (SE); Anders Nygard, Uppsala (SE)

(73) Assignee: Gyros AB, Uppsala (SE)

( * ) Notice: Subject to any disclaimer, the term of this patent is extended or adjusted under 35 U.S.C. 154(b) by 0 days.

(21) Appl. No.: 09/953,155

(22) Filed: Sep. 17, 2001

(65) Prior Publication Data

US 2003/0055576 A1 Mar. 20, 2003

(51) Int. Cl.$^7$ .............................................. G01N 30/00
(52) U.S. Cl. .................................. 702/31; 436/8
(58) Field of Search .......................... 702/19, 22, 23, 702/25, 30, 31, 32, 45, 50, 100; 436/8, 10, 55, 149, 150; 422/50, 107

(56) References Cited

U.S. PATENT DOCUMENTS 6,174,675 B1 * 1/2001 Chow et al. ................... 435/6
6,221,226 B1 * 4/2001 Kopf-Sill ..................... 204/602
6,294,063 B1 * 9/2001 Becker et al. ............... 204/450
6,495,369 B1 * 12/2002 Kercso et al. ................ 436/47

FOREIGN PATENT DOCUMENTS

WO    WO 00/58719    10/2000

* cited by examiner

Primary Examiner—Patrick Assouad
Assistant Examiner—Edward Raymond
(74) Attorney, Agent, or Firm—Birch, Stewart, Kolasch & Birch, LLP

(57) ABSTRACT

The invention can be described as a Method Handler (MH), which consists of several parts used to check and create different methods for microfluidic instruments. The part that creates methods can be called the Method Editor (ME). It is used to create a scheme of operations that together with the instrument builds up an application for a specific disc type. MH also checks if a method is executable on a specific instrument. This is done in a part called Batch Run (BR).

14 Claims, 4 Drawing Sheets

METHOD EDITOR

FIELD OF THE INVENTION

The present invention relates to a process for providing a dynamic method set including methods associated to a special microfluidic device type used in a microfluidic system. The present invention also relates to a computer program product, a computer program element and a carrier comprising the computer program product.

BACKGROUND OF THE INVENTION

The term "microfluidic" refers to a system or device having one or a network of chambers and/or channels, which have micro scale dimensions, e.g., having at least one cross sectional dimension in the range from about 0,1 $\mu$m to about 500 $\mu$m. Microfluidic substrates are often fabricated using photolithography, wet chemical etching, injection-molding, embossing, and other techniques similar to those employed in the semiconductor industry. The resulting devices can be used to perform a variety of sophisticated chemical and biological analytical techniques.

Microfluidic analytical systems have a number of advantages over conventional chemical or physical laboratory techniques. For example, microfluidic systems are particularly well adapted for analyzing small sample sizes, typically making use of samples on the order of nanoliters and even picoliters. The channel defining substrates may be produced at relatively low cost, and the channels can be arranged to perform numerous analytical operations, including mixing, dispensing, valving, reactions, detections, electrophoresis, and the like. The analytical capabilities of microfluidic systems are generally enhanced by increasing the number and complexity of network channels, reaction chambers, and the like.

Substantial advances have recently been made in the general areas of flow control and physical interactions between the samples and the supporting analytical structures.

Flow control management may make use of a variety of mechanisms, including the patterned application of voltage, current, or electrical power to the substrate (for example, to induce and/or control electrokinetic flow or electrophoretic separations). Alternatively, fluid flows may be induced mechanically through the application of differential pressure, acoustic energy, or the like. Selective heating, cooling, exposure to light or other radiation, or other inputs may be provided at selected locations distributed about the substrate to promote the desired chemical and/or biological interactions. Similarly, measurements of light or other emissions, electrical/electrochemical signals, and pH may be taken from the substrate to provide analytical results. As work has progressed in each of these areas, the channel size has gradually decreased while the channel network has increased in complexity, significantly enhancing the overall capabilities of microfluidic systems.

The microfluidics technologies/devices are capable of controlling and transferring tiny quantities of liquids to allow biological assays to be integrated and accomplished on a small scale.

Microfluidics is the miniaturization of biological separation and assay techniques to such a degree that multiple "experiments" can be accomplished on a "chip" small enough to fit in the palm of your hand. Tiny quantities of solvent, sample, and reagents are steered through narrow channels on the chip, where they are mixed and analyzed by such techniques as electrophoresis, fluorescence detection, immunoassay, or indeed almost any classical laboratory method.

Today a number of products varying in many respects are available. Laboratory chips may be made from plastic, glass, quartz or even silicon. The fluid may be driven by centrifugal forces, mechanical pressure or vacuum pumps, by inertia, or by one of several electrical methods; fluid flow can be diverted around the chip by mechanical valves, surface tension, voltage gradients, or even electromagnetic forces.

In the technique of using centrifugal forces to drive the fluid a disc that can be spinned is used. Some discs have been of the same physical format as conventional CDs. Samples are placed near the center of the disc and centrifugal forces, created as the disc rotates, push them out through channels cut into the plastic, circumventing the need to design sophisticated electrokinetic or mechanical pumping structures.

As will become evident in the forth-coming description the present invention is in particular applicable to (but not limited to) micro-analysis systems that are based on microchannels formed in a rotatable, usually plastic, disc, often called a "lab on a chip". Such discs can be used to perform analysis and separation on small quantities of fluids. In order to reduce costs it is desirable that the discs should be not restricted to use with just one type of reagent or fluid but should be able to work with a variety of fluids.

Furthermore it is often desirable during the preparation of samples that the disc permits the user to dispense accurate volumes of any desired combination of fluids or samples without modifying the disc. A microanalysis device for fluids provided in a rotatable disc is described e.g. in WO-01/46465

One general object of present invention is to increase the performance of a microfluidic system.

A more specific object of the present invention is to provide powerful tools when creating and performing various processes including sample preparation, treatment of liquids, various chemical and biochemical steps etc in a microfluidic device.

SUMMARY OF THE INVENTION

The invention can be described shortly as a method-developing tool, which consists of several parts used to check and create different methods for microfluidic instruments. The part that creates methods can be called the Method Editor (ME). It is used to create a scheme of operations that together with the instrument builds up an application for a specific microfluidic device type. The method-developing tool also checks if a method is executable on a specific instrument. This is done in a part called Batch Run (BR).

The above-mentioned objects are achieved by a process, a computer program product, a computer program element, and carrier according to the independent claims or by any other means suggested herein.

Preferred embodiments are set forth in the dependent claims.

Advantages provided by the present invention are that it offers a faster, more cost effective, more systematic and logical process for developing methods for microfluidic systems. The invention also offers a good survey and handling of available operations and developed methods.

BRIEF DESCRIPTION OF THE DRAWINGS

FIG. 3b is a flowchart illustrating an embodiment of a process that could be added to the process according to FIG. 3a.

DETAILED DESCRIPTION OF PREFERRED EMBODIMENTS

The present invention relates to a process for providing a dynamic method set including methods associated to a special microfluidic device type used in a microfluidic system. The present invention also relates to a computer program product, a computer program element and a carrier comprising the computer program product.

A microfluidic system may comprise a control unit and a microfluidic instrument. Such a system is called a Stand Alone System. Each system has its *own data and operates completely stand alone. The interaction with the system may be performed at an associated Personal Computer (PC).

Another system can be considered as a group of instruments plus a common persistent storage location, e.g. database. Many instruments can operate on the same set of data (Method Data, Microfluidic Device Data, etc). All interaction with the system needs to be performed at an instrument connected computer. This second system is often called a Distributed Database Solution.

In a third solution, the distributed solution, the system is considered as a group of instruments, a common storage persistent storage location (database), and a number of clients. With this solution the same functionality as in the above-mentioned Distributed Database Solution is reached. In addition there will be a possibility to interact with the system from non instrument connected computers. Examples of additional provided functionality are:

Remote monitoring of instruments.

Perform functions that are not instrument specific (Method Development, Evaluation of processed data. Etc)

With this third solution it is possible to control (Start, Pause, Abort) the processing remotely, that is, from a non instrument connected computer.

An operator/user can control and monitor the performance of the microfluidic instrument from the control unit. The microfluidic instrument comprises of a number of different stations, each station being capable of performing one or a number of defined operations. Different types of microfluidic instruments consist of different kinds of stations or number of stations. Therefore, some operations will not be provided for or applicable on a certain type of microfluidic instrument.

The operations are initiated from the control unit.

Figure 1:
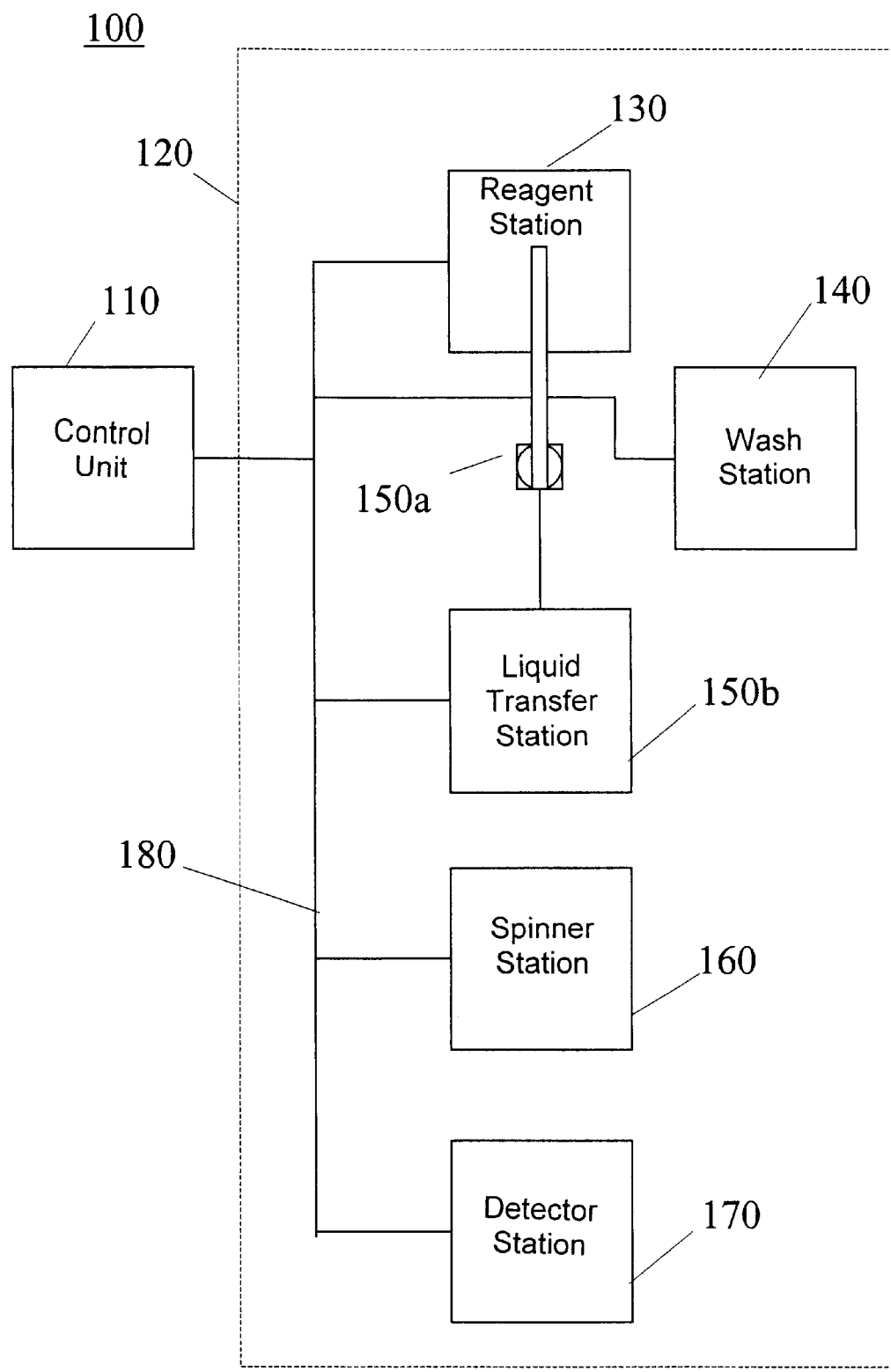
FIG. 1 is a block diagram depicting schematically a microfluidic system.

FIG. 1 is a block diagram depicting schematically a microfluidic system 100 that includes a control unit 110 and an instrument 120 comprising a sample and reagent station 130, a wash station 140, a liquid transfer station 150, at least one station 160 for implementing transport of liquid within the microfluidic device e.g., a spinner station and a detector station 170.

The control unit 110 may be one or more computers outside the instrument and/or one or more central processors within the instrument. The control unit is connected to the instrument 120 and its different stations via a conductor or data bus 180 and operation orders are transmitted either as electrical or optical signals or included in a suitable predetermined protocol to hardware circuits distributed between the stations.

The sample and reagent station 130 comprises means for storing samples, reagents or other liquids. Said samples, reagents or other liquids is stored in some kind of container, such as a micro plate or multiwell plate, a test tube rack or a test tube. Said plate is designed as a matrix of small containers or wells. Said plate can have different sizes depending on the number of wells. The container may be loosely fixed at a container holder, for instance a so called carousel, which is a circular revolving plate.

The liquid transfer station 150 has a robot 150a that transfer at least one sample or any other predetermined liquid aliquot at a time from the sample and reagent station 130 to a microfluidic device, for instance in the form of a disc that can be spinned. The station have means for transfer of liquid samples, and other liquids, for instance a number of injection needles connected to syringe pumps or a number of solid pins may be used for the transfer of samples. Said needles and pins may be configured in different numbers of rows and columns having different distance between the tips in both directions. Another alternative is the microdispensor described in WO 9701085.

Said needles and pins may or may not be washed in a wash solution between the transfers of samples and reagents. Washing is done by means placed in a wash station 140.

The liquids dispensed to a microfluidic device are transported within the device by means associated with the station 160 for implementing liquid transport. This station may be a spinner station in case the the microfluidic device is adapted to permit liquid transport caused by spinning. The result of a process carried out within the microfluidic device is determined by means for detecting (a detector) which is located in a detector station 170.

Figure 2:
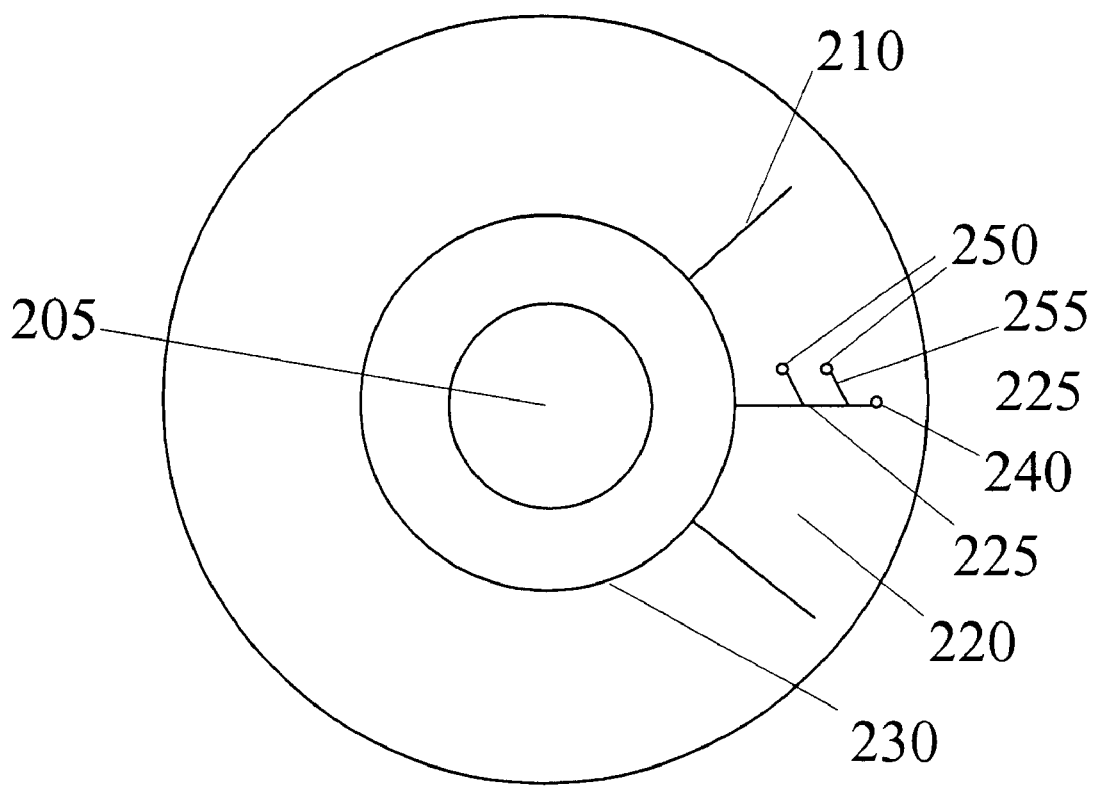
FIG. 2 is a schematic picture of a microfluidic device in form of a disc.

FIG. 2 is a schematic picture of a microfluidic disc 200. A rotatable disc is earlier described e.g. in WO-01/46465. The disc has a central recess 205 for a disc holder. Samples may be placed near the center of the disc and centrifugal forces, created as the disc rotates, may push them out through channels 210 cut into the plastic, circumventing the need to design sophisticated electrokinetic or mechanical pumping structures. Only one section 220 is depicted on the illustrated disc 200. A section on a disc is a group of microstructures 225 that are connected to a common distribution channel 230. A microstructure is a system of microchannels, which is used to perform a process protocol on a sample. A number of structures or channels 210 extend, for instance radially, from the common distribution channel 230 and ends in a detection position 240 where detection may occur. Inlet positions 250 are distributed along the channels. A small channel 255 extends from the inlet 250 and connects to said micro channel 210. Samples, liquids and reagent may be dispensed here.

As shown in FIG. 1, each of said stations is connected to the control unit 110 and controlled and monitored from the control unit 110 by means of a number of operations. A software operation is defined as a logical group of hardware instructions, which are performed to accomplish a certain function, such as:

Implementing transport of liquid, for instance spinning the device if the device is in the form of a disc that can be spinned in order to induce liquid flow.

Sample transfer to a specific common distribution channel or a specific microstructure.

Reagent transfer to a specific common distribution channel or a specific microstructure.

Position the microfluidic device.

Incubate the liquids at a certain position in the microstructures for a specific time.

Detection, i.e. detection of the results of the method carried out in the microfluidic device.

An operation may consist of a number of steps. A step is a non-dividable instruction, such as a ramp in a spin operation. A set can be constituted by putting together a number of these operations in a desired order. Such a set is defined as a method and controls all parts conducted within the instrument. It prescribes a type of microfluidic device and defines a set of actions, operations. It may prescribe halting for conducting steps outside the instrument, for instance incubations at constant temperature when the method concerns cell culturing.

As stated above, the present invention relates to a process for providing a dynamic method set including methods associated to a special microfluidic device type used in a microfluidic system. It is a generic tool in the meaning that it supports a method developer to build methods for any application, i.e. it can support all operations that are to be performed within the instrument.

The invention can be described as a Method Handler (MH), which consists of several parts used to check and create different methods. The part that creates methods can be called the Method Editor (ME). It is used to create a scheme of operations that together with the microfluidic device forms an application for a specific microfluidic device type. MH also checks if a method is executable on a specific instrument. This is done in a part called Batch Run (BR).

The method itself describes an application from a logical point of view, i.e. the sequence of operations, how to perform them, etc. The scheme of operations that builds up a method has no knowledge if it can be executed on a certain instrument. The ME is responsible for checking that a method is executable from a logical point of view.

The BR is responsible for checking if the method is executable on a specific instrument from a physical and chemical point of view and if the settings of the instrument are acceptable and appropriate.

Figure 3A:
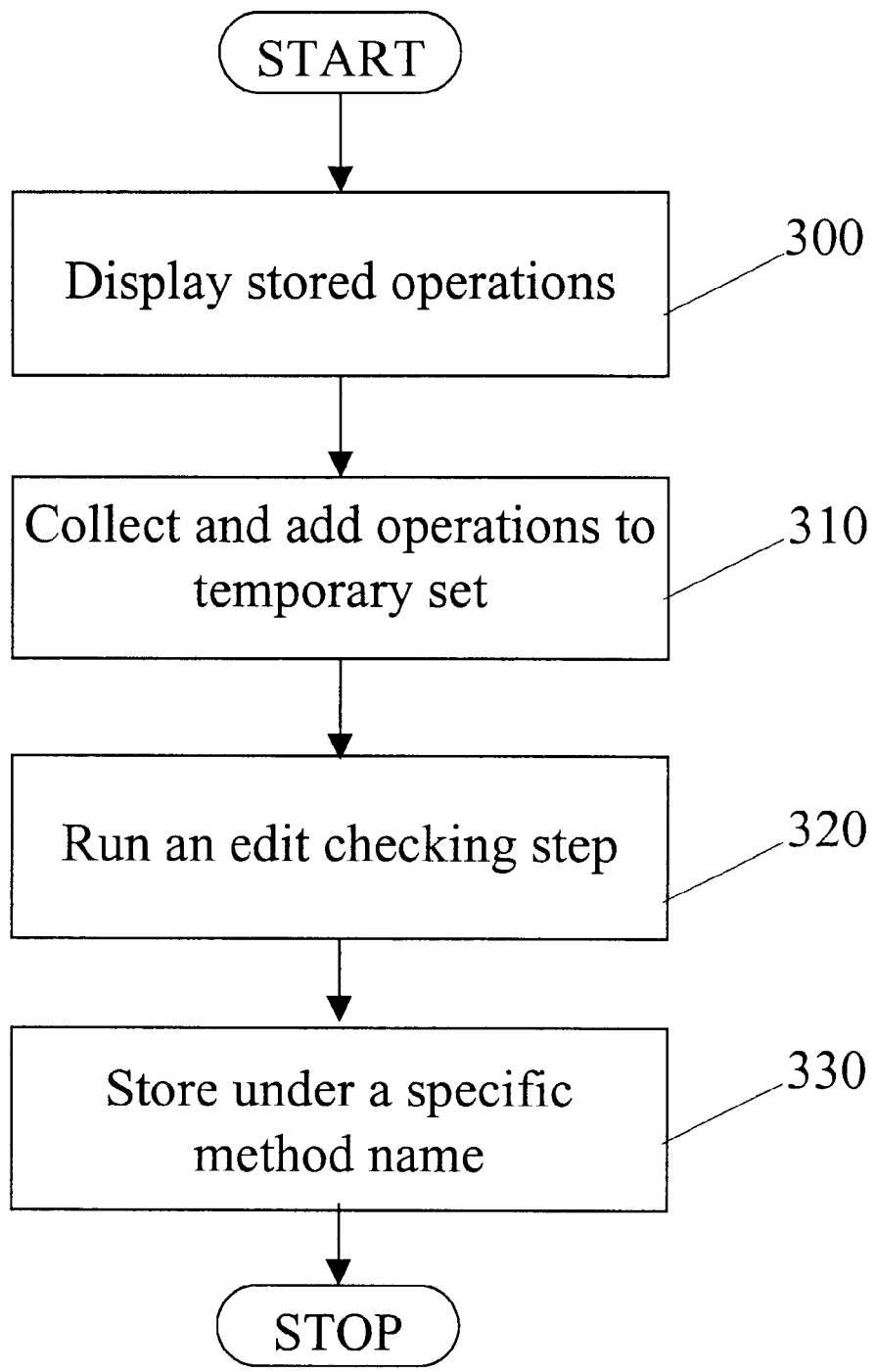
FIG. 3a is a flowchart illustrating an embodiment of the process according to the invention.

An embodiment of the Method Handling tool and the process according to the invention will now be described in more detail with reference to the flowchart in FIG. 3a. The process includes following steps:

step 300: displaying predetermined operations of stored predetermined microfluidic device operations on a display or screen;

step 310: collecting a number of predetermined operations from said stored and displayed predetermined microfluidic device operations and adding said collected predetermined operations to a temporary set;

step 320: running an edit checking step for accepting or rejecting said temporary set of operations, wherein said edit checking step makes use of a set of rules related to the special microfluidic device type and to other logical rules;

step 330: storing said checked and accepted microfluidic device type set of operations, i.e. said temporary set in accepted form, under a specific method name and in a format applicable for transfer to said dynamic method set.

Further, some of the collected and added operations require additional information or data, here defined as operation settings. In step 315, between step 310 and 320, required operation settings associated to an operation are inquired and acquired.

The invented process can be performed on an ordinary personal computer having a display or screen and input means, for instance a mouse and a keyboard. The method handler comprises a user interface for displaying predetermined operations of stored predetermined microfluidic device operations on a display or screen. The user interface provides a window having a button or tab for each selectable operation. When the user selects an operation, he/she has only to point at the desired operation button and click the button using a mouse button. As the user selects operations, the computer or processor collects the corresponding predetermined microfluidic device operations from a computer readable storage or memory or server or other medium in the order determined by the user/method developer, adding said collected predetermined operations in said order to a temporary set in a database or an allocated memory area in a computer readable storage or memory or server or other medium. For some of the operations, the method handler software will inquire for completing information and instructions, operation settings, e.g. spinning velocity or spinning time. When the user is finished with the selection of operation, the method handler software will run an edit checking step for accepting or rejecting said temporary set of operations. Said edit checking step makes use of a set of rules and conditions related to the special microfluidic device type and to other logical rules. If the user has made mistakes in filling in the completing information, such as operation settings, and instructions, the edit checking step will reject the temporary set or ask for completing information. When the temporary set is accepted it is stored under a specific method name and in a format applicable for transfer to said dynamic method set.

Said associated dynamic method set is dynamic in that the application specific methods and/or operations may be added or amended or deleted if needed.

As stated above, the invention uses a set of rules and conditions to determine if the method is executable. Basically a check if all necessary information are in place.

Here follows, as an example, an non-exhaustive list of suitable rules:

If spin operation is selected, is spin step defined?

Are positions on the microfluidic device selected?

Are necessary liquids defined?

Figure 3B:
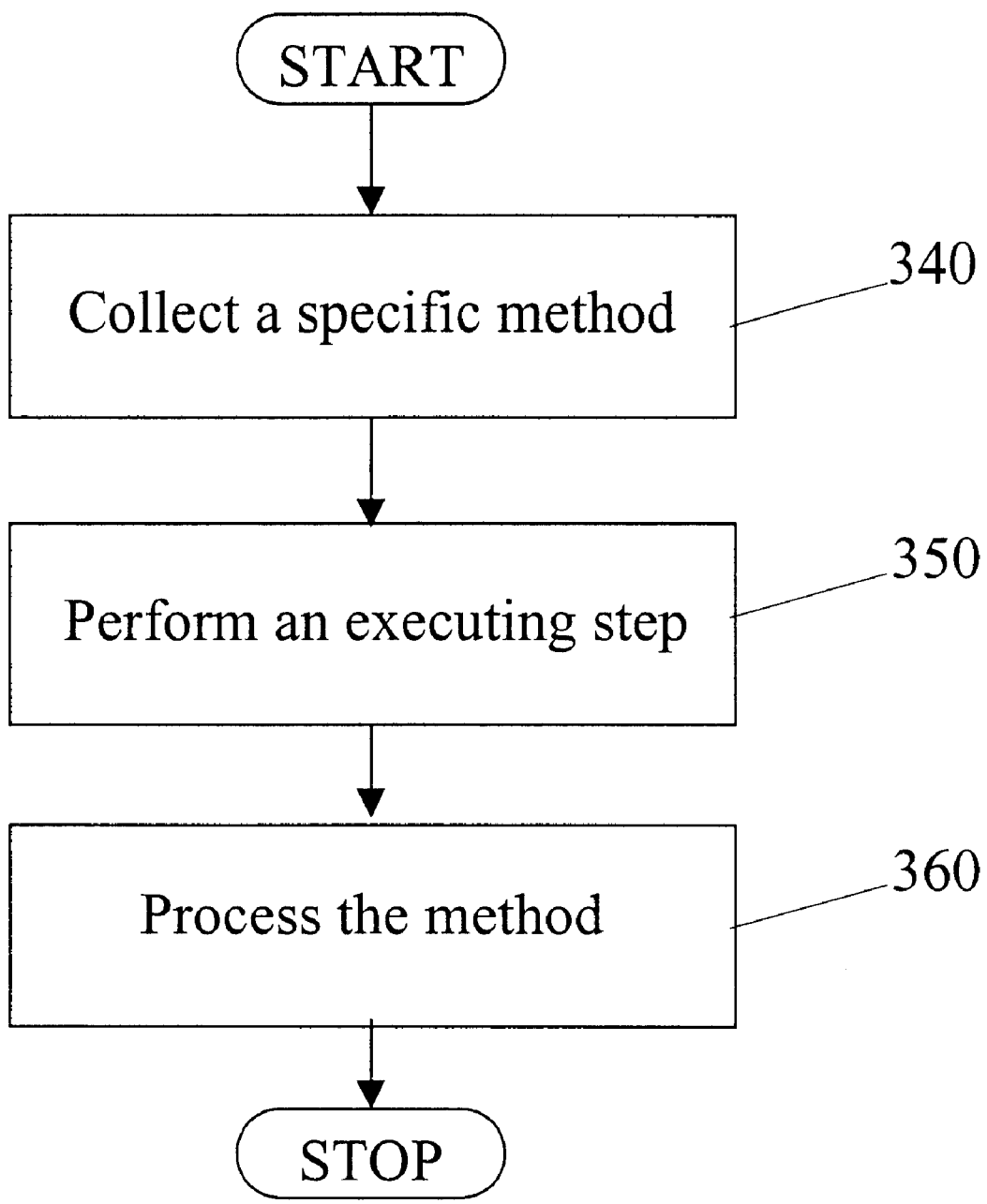

Further, the invented process includes an executing step (Batch Run) comprising the following steps, as illustrated in the flowchart in FIG. 3b:

step 340: collecting one set of microfluidic device type operations associated with a specific method name;

step 350: performing the executing checking step by applying a set of rules and conditions related to the microfluidic system where the set of operations is to be processed, and;

step 360: processing the microfluidic device with the microfluidic system using the set of operations.

When the user (method developer) selects a specific method, the user will initiate an executing step of the method handler tool. The method handler software causes the computer to perform a collection of one set of microfluidic device type operations associated with the selected specific method name and an execution of a checking step by applying a set of rules and conditions related to the microfluidic system where the set of operations is to be processed. If the user has made mistakes in filling in the completing information and instructions or the selected method is not applicable on the present system instrument or its configuration, the Batch Run checking step will reject the method. The things to check can be:

Does the instrument have the right hardware and hardware configuration and settings to perform the different operations?

Is the method executable? I.e. does it contain all information needed to execute the method.

Have the right liquids been loaded?

If the method is accepted, the system can use the microfluidic device within the microfluidic system for processing the set of operations defined by the method.

Here follows a short presentation of how the Method Handler tool is used. A method developer using the invented Method Handler tool may take following steps:

Chose type of microfluidic device;

Build up the method (or sequence of operations) from information related to the type of microfluidic device;

Apply a set of rules in ME checking step;

Save checked method and then distribute storage medium with checked method or distribute checked method via internet, e.g. user may download from provider server, to user/customer.

When the method shall be executed the MH checks, by applying Batch Run rules, if the connected instrument can process the selected method.

A user receives the method stored at a storage medium or downloads it from internet or creates it. A BR checking step is then performed where a BR set of rules is applied, said set of rules are related to the instrument. If accepted, it is only to run and use the method.

The invention also relates to a computer program product stored at a computer program product readable means, having thereon computer program code means, when said program is loaded, to make a computer to perform the process according to any of claims 1–5.

The invention also relates to a computer program element for providing a dynamic method set including methods associated to a special microfluidic device type used in a microfluidic system. The computer program code comprises at least following computer executable computer program elements:

a user interface element, said user interface element being capable of displaying predetermined operations stored in a predetermined microfluidic device operations storage;

an operation collecting element, said collecting element being capable of collecting a number of predetermined operations from said stored and displayed predetermined microfluidic device operations;

an adding element, said adding element being capable of adding said collected predetermined operations to a temporary set;

an edit checking step element, said edit checking element being capable of running an edit checking step for accepting or rejecting said temporary set of operations, wherein said edit checking step makes use of a set of rules related to the special microfluidic device type and to other logical rules;

a storing element, said storing element being capable of storing said checked and accepted microfluidic device type set of operations under a specific method name and in a format applicable for transfer to said dynamic method set.

Further, the computer program element comprises:

a method collecting element, said element being capable of collecting one set of microfluidic device type operations associated with a specific method name;

an executing checking step element, said element being capable of performing the executing checking step by applying a set of rules and conditions related to the microfluidic system where the set of operations is to be processed, and;

a processing step element, said element being capable of processing the microfluidic device with the microfluidic system using the set of operations.

The computer program element may also comprise an inquiring and acquiring element, said element being capable inquiring and acquiring required operation settings associated to a collected and added operation.

The present invention also relates to a carrier having thereon at least one dynamic method set including methods associated to a special microfluidic device type used in a microfluidic system comprising at least one central processor and storage means for computer program code. Each method in said dynamic method set is accepted for a special microfluidic device type and defined by a specific method name and said method comprises a number of operations causing the microfluidic system to perform said operations in a predetermined order. The carrier may be a record medium, a computer memory, a Read-Only Memory or an electrical carrier signal.

The process may also contain additional steps, for instance a step in which a method after the edit checking step, either before or after the storing step, is accepted in the sense that the method becomes static without possibility to further edit or remove it from the dynamic method set. The computer program product, the computer program element and the carrier may comprise the corresponding feature.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A process for providing a dynamic method set for treatment and/or analyses of samples, including methods associated to a special microfluidic device type used in a microfluidic system comprising at least one central processor and storage means for computer program code, the of:

displaying predetermined operations of stored predetermined microfluidic device operations for treatment and/or analyses of samples;

collecting a number of predetermined operations from said stored and displayed predetermined microfluidic device operations and adding said collected predetermined operations to a temporary set;

running an edit checking step for accepting or rejecting said temporary set of operations for treatment and/or analyses of samples, wherein said edit checking step makes use of a set of rules related to the special microfluidic device type and to other logical rules;

storing said checked and accepted microfluidic device type set of operations under a specific method name and in a format applicable for transfer to said dynamic method set.

2. The process according to claim 1, wherein said associated dynamic method set is dynamic in that application specific methods and/or operations may be added/amended/deleted if needed.

3. The process according to claim 1, wherein said process further includes an executing step comprising the following steps:
- collecting one set of microfluidic device type operations associated with a specific method name;
- performing an executing checking step by applying a set of rules and conditions related to the microfluidic system where the set of operations is to be processed; and
- processing the microfluidic device with the microfluidic system using the set of operations.

4. The process according to claim 1, wherein said operations includes at least one of the following operations:
- spinning the microfluidic device;
- transferring a sample to a specific common channel or microstructure;
- transferring a reagent to a specific common channel or microstructure;
- positioning the microfluidic device;
- holding the microfluidic device for a specific time;
- incubating the microfluidic device for a specific time; and
- detecting a composition of the sample.

5. The process according to claim 1, wherein said process includes the following step:
- inquiring and acquiring of required operation settings associated to a collected and added operation.

6. A computer program product stored at a computer program product readable means, said program product being adapted to perform the process according to any of claims 1–5.

7. A computer program element for providing a dynamic method set for treatment and/or analyses including methods associated to a special microfluidic device type used in a microfluidic system, the computer program code comprising at least following computer executable computer program elements:
- a user interface element, said user interface element being capable of displaying predetermined operations for treatment and/or analyses stored in a predetermined microfluidic device operations storage means;
- an operation collecting element, said collecting element being capable of collecting a number of predetermined operations from said stored and displayed predetermined microfluidic device operations;
- an adding element, said adding element being capable of adding said collected predetermined operations to a temporary set;
- an edit checking step element, said edit checking element being capable of running an edit checking step for accepting or rejecting said temporary set of operations, wherein said edit checking step makes use of a set of rules related to the special microfluidic device type and to other logical rules;
- a storing element, said storing element being capable of storing said checked and accepted microfluidic device type set of operations under a specific method name and in a format applicable for transfer to said dynamic method set.

8. The computer program element according to claim 7, further including:
- a method collecting element, said element being capable of collecting one set of microfluidic device type operations associated with a specific method name;
- an executing checking step element, said element being capable of performing the executing checking step by applying a set of rules and conditions related to the microfluidic system where the set of operations is to be processed, and;
- a processing step element, said element being capable of processing the microfluidic device with the microfluidic system using the set of operations.

9. A computer program element according to claim 7,
further including and inquiring and acquiring element, said inquiring and acquiring element being capable inquiring and acquiring required operation settings associated to a collected and added operation.

10. A carrier having thereon at least one dynamic method set for treatment and/or analyses of samples including methods associated to a special microfluidic device type used in a microfluidic system comprising at least one central processor and storage means for computer program code, each method in said dynamic method set being accepted for a special microfluidic device type and defined by a specific method name and said method comprises a number of analytical operations causing the microfluidic system to perform said analytical operations in a predetermined order.

11. The carrier according to claim 10, wherein said carrier is a recording medium.

12. The carrier according to claim 10, wherein said carrier is a computer memory.

13. The carrier according to claim 10, wherein said carrier is a Read-Only Memory.

14. The carrier according to claim 10, wherein said carrier is an electrical carrier signal.

* * * * *